(12) United States Patent
Sheverev

(10) Patent No.: US 7,408,360 B2
(45) Date of Patent: Aug. 5, 2008

(54) GAS DETECTION AND IDENTIFICATION APPARATUS AND METHOD

(76) Inventor: Valery A. Sheverev, 7 Tenney Rd., West Orange, NJ (US) 07052

( * ) Notice: Subject to any disclaimer, the term of this patent is extended or adjusted under 35 U.S.C. 154(b) by 0 days.

(21) Appl. No.: 11/431,283

(22) Filed: May 10, 2006

(65) Prior Publication Data

US 2007/0273384 A1    Nov. 29, 2007

(51) Int. Cl.
  *G01N 27/62*    (2006.01)
(52) U.S. Cl. .................................................. 324/464
(58) Field of Classification Search .............. 324/464
  See application file for complete search history.

(56) References Cited

U.S. PATENT DOCUMENTS 6,900,734 B2    5/2005    Duan
2004/0245993 A1*   12/2004    Bonne ........................ 324/464

OTHER PUBLICATIONS

V.A. Sheverev, N.A. Khromov, D.R. Kojiro Penning Ionization Electron Spectroscopy in Glow Discharge: Another Dimension for Gas Chromatography Detectors; Analytical Chemistry vol. 74, No. 21, Nov. 1, 2002 pp. 5556-5563.
G.A. Eiceman, J. Gardea-Torresdey, E. Overton, K. Carney, F. Dorman Gas Chromatography; Analytical Chemistry vol. 76, No. 12, Jun. 15, 2004 pp. 3387-3394.
N.B. Kolokolov, A.A. Kudrjavtsev, A.B. Blagoev Interaction Processes With Creation of Fast Electrons in the Low Temperature Plasma; Physica Scripta vol. 50, pp. 371-402 1994.
S.O. Akapo, J.-M.D. Dimandja, D.R. Kojiro, J.R. Valentin, G.C. Carle Gas chromatography in space; Journal of Chromatography A. 843 (1999) pp. 147-162.
V. Karanassions Microplasma for chemical analysis: analytical tools or research toys?; Spectrochimica Acta Part B 59 (2004) pp. 909-928.

* cited by examiner

*Primary Examiner*—Timothy J Dole
(74) *Attorney, Agent, or Firm*—Andrew L. Ney

(57) ABSTRACT

Gas detection and identification apparatus that receives a flow of a mixture of a carrier gas and an analyte gas and detects and identifies the components of the flowing gas mixture by Penning Ionization Electron Spectroscopy (PIES).

7 Claims, 5 Drawing Sheets

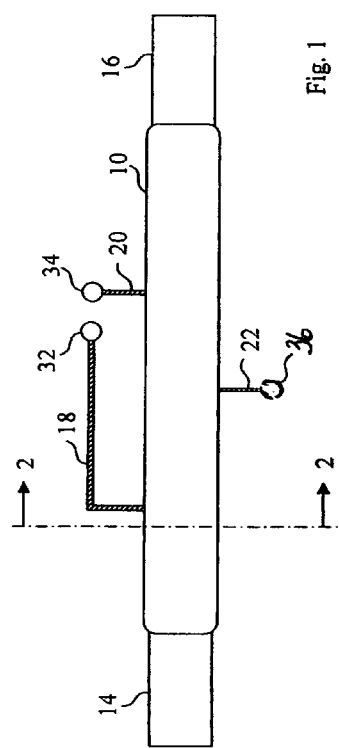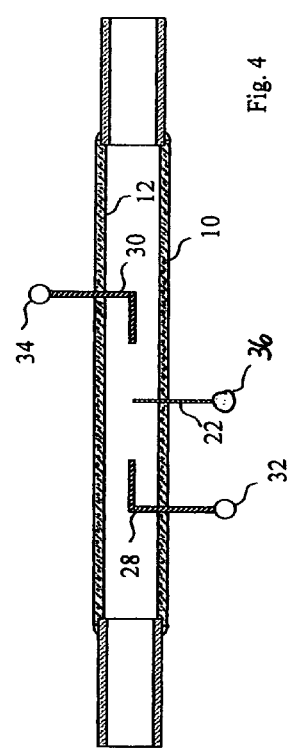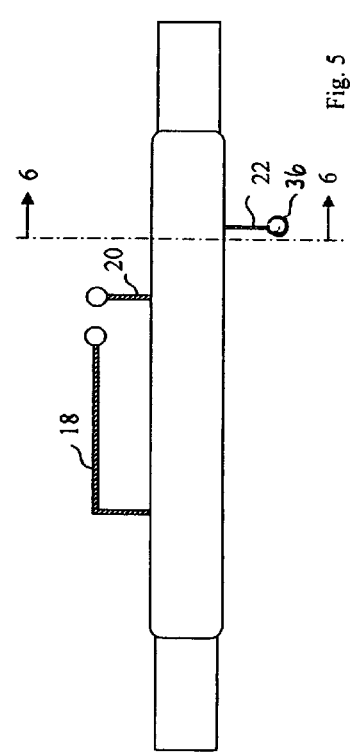

GAS DETECTION AND IDENTIFICATION APPARATUS AND METHOD

FIELD OF THE INVENTION

The present invention relates, in general, to an apparatus and a method for detecting the presence of one or more gases in a flowing gaseous fluid and, in particular, to a gas detection apparatus and method that detects the presence of flowing gases and identifies these gases by Penning Ionization Electron Spectroscopy (PIES).

BACKGROUND OF THE INVENTION

In recent years, there has been a clear trend to downscale analytical instruments and to realize such instruments on the chip-based format. Examples can be found in every branch of analytical science, but this trend is especially important for gas analysis given the shear size of the field and the importance in science and engineering, industrial process control, improved environmental practices, aerospace applications, and other areas. Modern applications require the detection and identification of a wide variety of chemical species over vast concentration ranges. The analysis often must be carried out under limited conditions utilizing minimal resources.

For example, control of pure industrial processes, such as plasma processing, requires continuous monitoring of the process environment and the detection and identification of a wide range of chemical species. This monitoring often must be carried out in very limited conditions of chemically aggressive environments. Techniques that utilize miniature, rugged, but sensitive, devices are a top priority in addressing these issues. Each process, however, presents its own unique set of analytical requirements. Analytical instrumentation possessing universal response and providing primary sample identification can minimize the number of required instruments and, therefore, is highly desired for industrial process control, as well as for other applications in modern science and technology.

The need for miniature detection technologies capable of sample identification is strong because such detection technologies can be fully integrated with a chip-based gas chromatograph forming a micro-total analysis system. The on-chip combination of a molecular-specific detector and a gas chromatograph would be suitable for many different applications and would provide the benefits of device downscaling: portability, low weight, low power consumption, fast analysis, radical reduction in carrier gas consumption, easy integration, and low cost of production.

Advances in analytical science have produced sensitive, but small, devices capable of detecting gases. Chemical sensors are examples of such devices. These sensors, although tiny and highly sensitive with a wide response range, do not provide sample identification information. Only a few analytical techniques, such as Mass Spectrometry (MS), Ion Mobility Spectrometry (IMS), and Optical Emission Spectrometry (OES), coupled with Gas Chromatography (GC/MS, GC/IMS, and GC/OES), provide independent identification of chemical species. Portable mass spectrometers are characterized by high detection limits and resolution and are capable of offering the speed required for fast and ultra-fast gas chromatography. However, these units are technically complex, heavy and bulky, and require vacuum and high voltage for operation.

With the advance of micro-plasma sources, OES, specifically molecular emission spectroscopy, has received significant attention in recent years as a technology than is applicable to in-field gas analysis. As with MS, this technology involves resolving a task of miniaturization of the optical spectrum detection system to on-chip standards that is similar in complexity to that of MS.

IMS continues to be considered a promising technique for on-chip integration because it does not require optics as does OES or high-vacuum equipment as does MS. Presently, however, portable IMS devices used as in-field monitors experience a number of problems related mostly to poor selectivity and memory effects. In addition, IMS instruments require significant amounts of carrier gas and require a source of ionization that complicates the design.

Penning Ionization Electron Spectroscopy in plasma (PIES) also has been utilized in analytical science. PIES provides direct molecular identification of gas mixture components. A PIES detector does not simply collect electrons produced by Penning ionization, as is the case with the non-selective Metastable Ionization Detector and other helium ionization type detectors such as IMS, but relies on the measurement, in a discharge afterglow plasma, of the energy electrons formed by Penning ionization. The electron energy spectrum produced contains peaks specific for each component of the sample gas. Because the ionization energy is specific to each molecular species, the resultant data can be used to directly identify each component. This PIES electron energy spectrum is developed by means of a single collector electrode placed in the glow discharge plasma.

To date, the analysis of chemical species by PIES analytical technology has been for stagnant gas in a sealed discharge cell. The prior art known to applicant is devoid of teachings or suggestions that PIES analytical technology can be applied to detect and identify the presence of one or more gases in a flowing gaseous fluid.

SUMMARY OF THE INVENTION

The present invention, based on Penning Ionization Electron Spectroscopy in glow discharge plasma, provides an analytical apparatus and method useful in detecting and identifying a wide range of chemical species present in a flowing gas mixture. The present invention measures the energy of electrons liberated by Penning Ionization in the afterglow of a gas discharge. The produced electron energy spectrum contains peaks specific for each component of the sample gas. Contrary to the above mentioned prior art technologies, Penning Ionization Electron Spectroscopy is relatively simple in implementation. The apparatus is similar to microplasma apparatus used in optical emission spectroscopy, mass spectroscopy, and ion mobility spectrometry, but, in accordance with the present invention, such equipment, with a minimal extension for an additional electrode, incorporates a source and an analyzer in the same volume thus providing an opportunity for true integration in an on-chip gas analyzer. The technical simplicity of PIES (e.g., no optics or ultra-high vacuum is required) and the capability to directly identify various species with high sensitivity make it ideal for miniature analytical instrumentation for in situ applications.

A gas detector, constructed in accordance with the present invention, includes an elongated tube having a through bore with means at a first end of the elongated tube for receiving in the through bore a flow of a mixture of a carrier gas and an analyte gas and means at a second end of the elongated tube for exhausting from the through bore the flow of the mixture of the carrier gas and the analyte gas. This gas detector also includes a pair of excitation electrodes and an electron collector electrode mounted to the elongated tube at selected locations along the length of the elongated tube so that the through bore is free of recesses. The excitation electrodes and the electron collector electrode are exposed to the flow of the mixture of the carrier gas and the analyte gas through the through bore. The excitation electrodes are adapted for connection to a source of excitation voltage for exciting the mixture of the carrier gas and the analyte gas and transforming the mixture of the carrier gas and the analyte gas into a plasma that contains excited atoms and molecules of the carrier gas and electrons at various excitation levels released from the analyte gas that travel in the plasma. The electron collector electrode is adapted for connection to a source of electron collection voltage that varies in level over time for selectively collecting at particular times those electrons traveling in the plasma that have excitation levels that exceed the levels of the electron collection voltage applied to the electron collector electrode at the particular times.

Gas detection and identification apparatus, constructed in accordance with the present invention, includes a gas detector comprising an elongated tube having a through bore, means at a first end of the elongated tube for receiving in the through bore a flow of a mixture of a carrier gas and an analyte gas, means at a second end of the elongated tube for exhausting from the through bore the flow of the mixture of the carrier gas and the analyte gas, and a pair of excitation electrodes and an electron collector electrode mounted to the elongated tube at selected locations along the length of the elongated tube. The excitation electrodes and the electron collector electrode are exposed to the flow of the mixture of the carrier gas and the analyte gas through the through bore. An excitation voltage source is connected to the excitation electrodes for applying an excitation voltage between the excitation electrodes to excite the mixture of the carrier gas and the analyte gas and to transform the mixture of the carrier gas and the analyte gas into a plasma that contains excited atoms and molecules of the carrier gas and electrons at various excitation levels released from the analyte gas that travel in the plasma. An electron collection voltage source is connected to the electron collector electrode for applying a voltage that varies in level over time to the electron collector electrode to selectively collect at particular times those electrons traveling in the plasma that have excitation levels exceeding the levels of the electron collection voltage applied to the electron collector electrode at the particular times. This gas detection and identification apparatus further includes means responsive to the electrons collected at the electron collector electrode for developing a spectrum of the electrons collected at different voltage levels of the electron collection voltage applied to the electron collector electrode.

BRIEF DESCRIPTION OF THE DRAWINGS

FIG. 1 is a side view of a first embodiment of a gas detector constructed in accordance with the present invention.

FIG. 4 is a sectional view of a third embodiment of a gas detector constructed in accordance with the present invention.

FIG. 5 is a side view of a fourth embodiment of a gas detector constructed in accordance with the present invention.

DETAILED DESCRIPTION OF THE INVENTION

Figure 2:
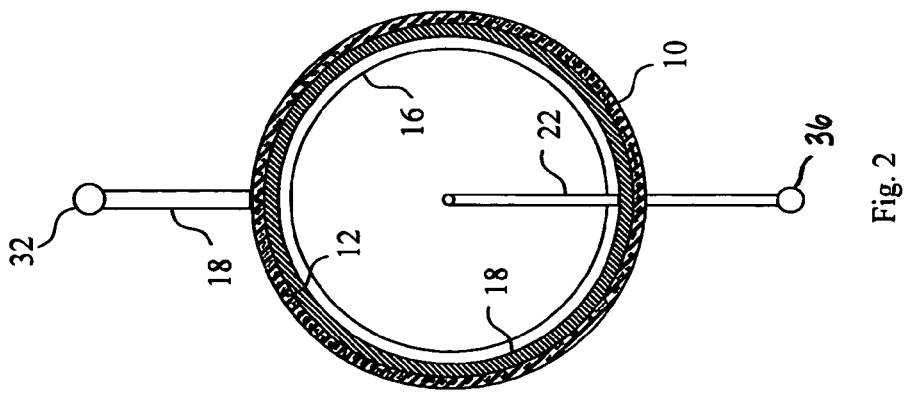
FIG. 2 is a sectional view, on an enlarged scale, of the FIG. 1 gas detector taken along line 2-2 of FIG. 1.

Referring to FIGS. 1 and 2, a gas detector, constructed in accordance with the present invention, includes an elongated tube 10 having a through bore 12. Tube 10 preferably is fabricated from glass, quartz, or a suitable ceramic.

The gas detector of FIGS. 1 and 2 also includes means at a first end of elongated tube 10 for receiving in through bore 12 a flow of a mixture of a carrier gas and an analyte gas and means at a second end of the elongated tube for exhausting from the through bore the flow of the mixture of the carrier gas and the analyte gas. Such means for receiving and exhausting the mixture of the carrier gas and the analyte gas can be conventional SWAGELOK couplings identified by reference numeral 14 at the input end of elongated tube 10 and reference numeral 16 at the output end of the elongated tube. As will be explained in greater detail in connection with FIGS. 7 and 8, the mixture of the carrier gas and the analyte gas flowing into through bore 12 of elongated tube 10 may be the output of an analytical instrument such as a gas chromatograph.

The gas detector of FIGS. 1 and 2 further includes a pair of excitation electrodes 18 (e.g., an anode) and 20 (e.g., a cathode) and an electron collector electrode 22 mounted to elongated tube 10 at selected locations along the length of the elongated tube so that through bore 12 is free of recesses that would otherwise form dead spaces in which the mixture of the carrier gas and the analyte gas might be trapped undesirably. For the embodiment of the present invention illustrated in FIGS. 1 and 2, electron collector electrode 22 is mounted between excitation electrodes 18 and 20. For the embodiment of the present invention illustrated in FIGS. 5 and 6, electron collector electrode 22 is mounted between the downstream excitation electrode 20 and the output or exhaust end of elongated tube 10.

Excitation electrodes 18 and 20 may take various forms. As illustrated in FIG. 2, anode electrode 18 extends circumferentially along a selected arc length of through bore 12, for example 360°, as illustrated in FIG. 2. Anode electrode 18 in FIG. 2, as well as cathode electrode 20, can be formed as coatings or platings deposited on the surface of through bore 12 that are connected to lead lines extending through the wall of elongated tube 10.

In an alternative arrangement, elongated tube 10 may be composed of two semicircular parts that have circumferential grooves in which anode electrode 18 and cathode electrode 20 are fitted or deposited with the two semicircular parts joined together along a gas tight joint. As with the embodiment of the present invention already described, the through bore of this two-part construction of the elongated tube, after the excitation electrodes and the electron collector electrode are mounted, is preferably free of recesses or dead spaces. The excitation electrodes, fitted or deposited into the semicircular parts, either are flush with the through bore surface or extend into the through bore.

Figure 3:
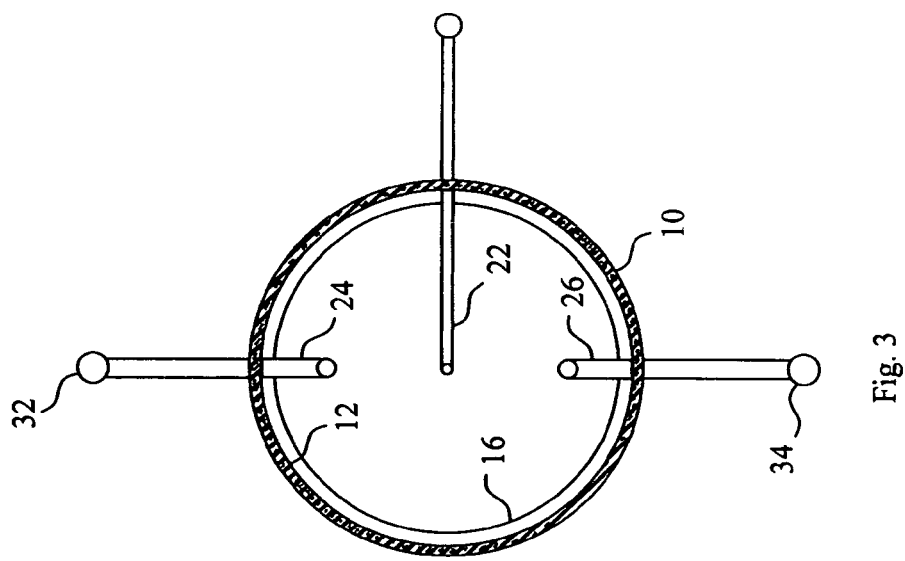
FIG. 3 is a sectional view of a second embodiment of a gas detector constructed in accordance with the present invention.

FIG. 3 is a sectional view of a second embodiment of a gas detector constructed in accordance with the present invention. In the FIG. 3 embodiment of the present invention, each of the excitation electrodes 24 and 26 extends radially through the wall of elongated tube 10 from outside the elongated tube to through bore 12.

FIG. 4 is a sectional view of a third embodiment of a gas detector constructed in accordance with the present invention. In the FIG. 4 embodiment of the present invention, each of the excitation electrodes 28 and 30 extends axially of through bore 12.

As indicated above, through bore 12 is free of recesses that would otherwise form dead spaces in which the mixture of the carrier gas and the analyte gas might be trapped undesirably. Thus, the anode electrode and cathode electrode of a gas detector constructed in accordance with the present invention should be flush with the surface of through bore 12 or extend into the through bore as illustrated in FIGS. 2, 3 and 4. In this way, the excitation electrodes are exposed to the flow of the mixture of the carrier gas and the analyte gas through bore 12.

Excitation electrodes 18 and 20 in FIGS. 1 and 2, excitation electrodes 24 and 26 in FIG. 3, and excitation electrodes 28 and 30 in FIG. 4 are adapted for connection to a source of excitation voltage. The connections of the excitation electrodes to the source of excitation voltage are represented by terminals 32 and 34. As will be explained in connection with the description of FIGS. 7 and 8, with the excitation electrodes connected to a source of excitation voltage, the mixture of the carrier gas and the analyte gas is excited and transformed into a plasma that contains excited atoms and molecules of the carrier gas and electrons at various excitation levels released from the analyte gas that travel in the plasma.

Figure 6:
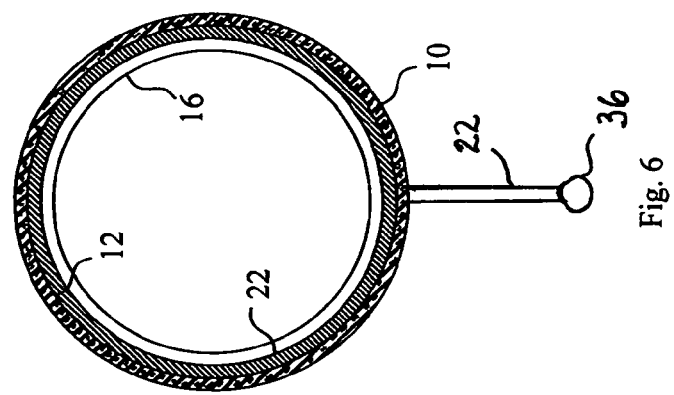
FIG. 6 is a sectional view, on an enlarged scale, of the FIG. 5 gas detector taken along line 6-6 if FIG. 5.

Similar to the excitation electrodes, electron collector electrode 22 may take different forms and be mounted to elongated tube 10 in different ways. In FIGS. 2 and 3, electron collector electrode 22 extends radially through the wall of elongated tube 10 from outside the elongated tube to through bore 12. In FIG. 6, electron collector electrode 22 extends circumferentially along a selected arc length of through bore 12, for example 360° as illustrated in FIG. 6.

Electron collector electrode 22 is adapted for connection to a source of electron collection voltage. The connection of the electron collector electrode to the source of electron collection voltage is represented by a terminal 36. As will be explained in connection with the description of FIGS. 7 and 8, with electron collector electrode 22 connected to a source of electron collection voltage, electrons traveling in the plasma are selectively collected at the electron collector electrode.

In the FIG. 1 embodiment of the present invention, electron collector electrode 22 is located in the plasma formed between anode electrode 18 and cathode electrode 20 and collects electrons from the plasma formed between the anode electrode and the cathode electrode. In the FIG. 5 embodiment of the present invention, electron collector electrode 22 is located downstream of cathode electrode 20 and collects electrons from the plasma that flows from between the anode electrode and the cathode electrode, where the plasma is formed, to downstream of the cathode electrode. A comparison of the different operating conditions of the FIG. 1 embodiment of the present invention and the FIG. 5 embodiment of the present invention is provided with reference to FIGS. 7, 8, 9A, and 9B.

Figure 7:
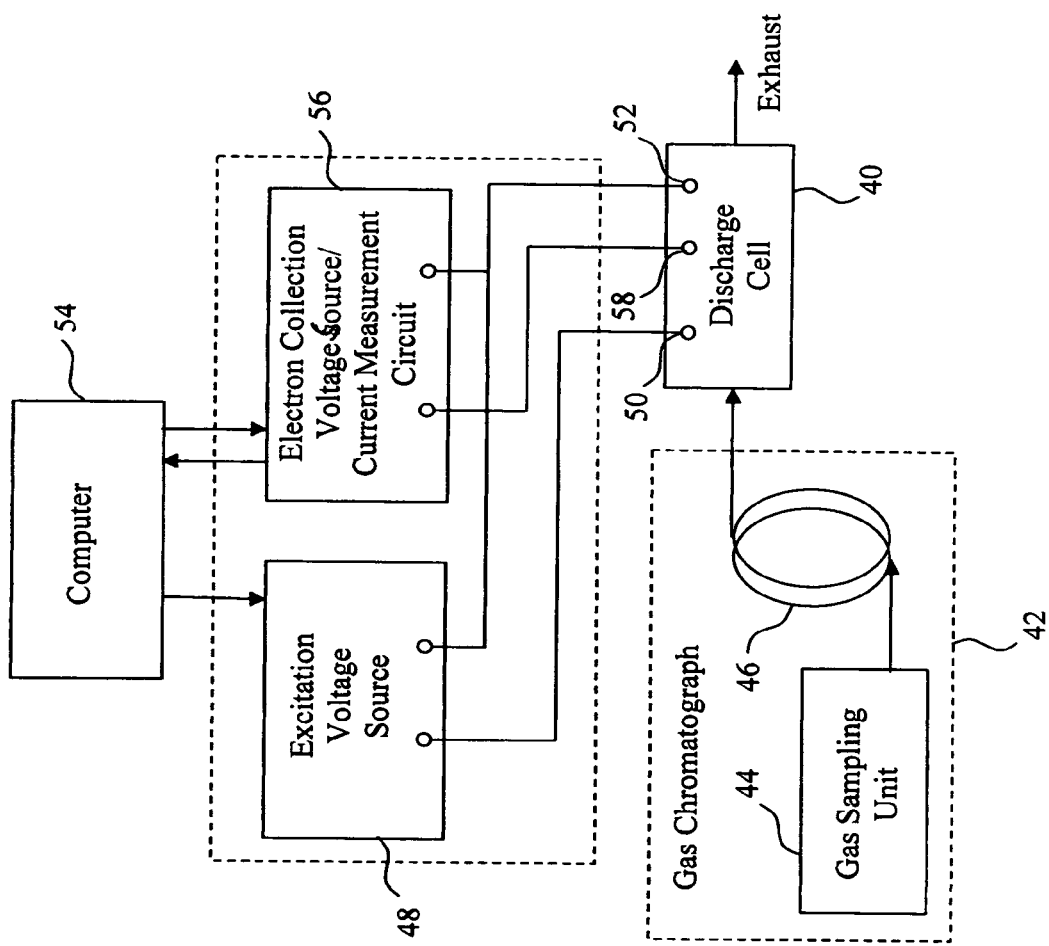
FIG. 7 is a block diagram of gas analyzer apparatus constructed in accordance with the present invention.
Figure 8:
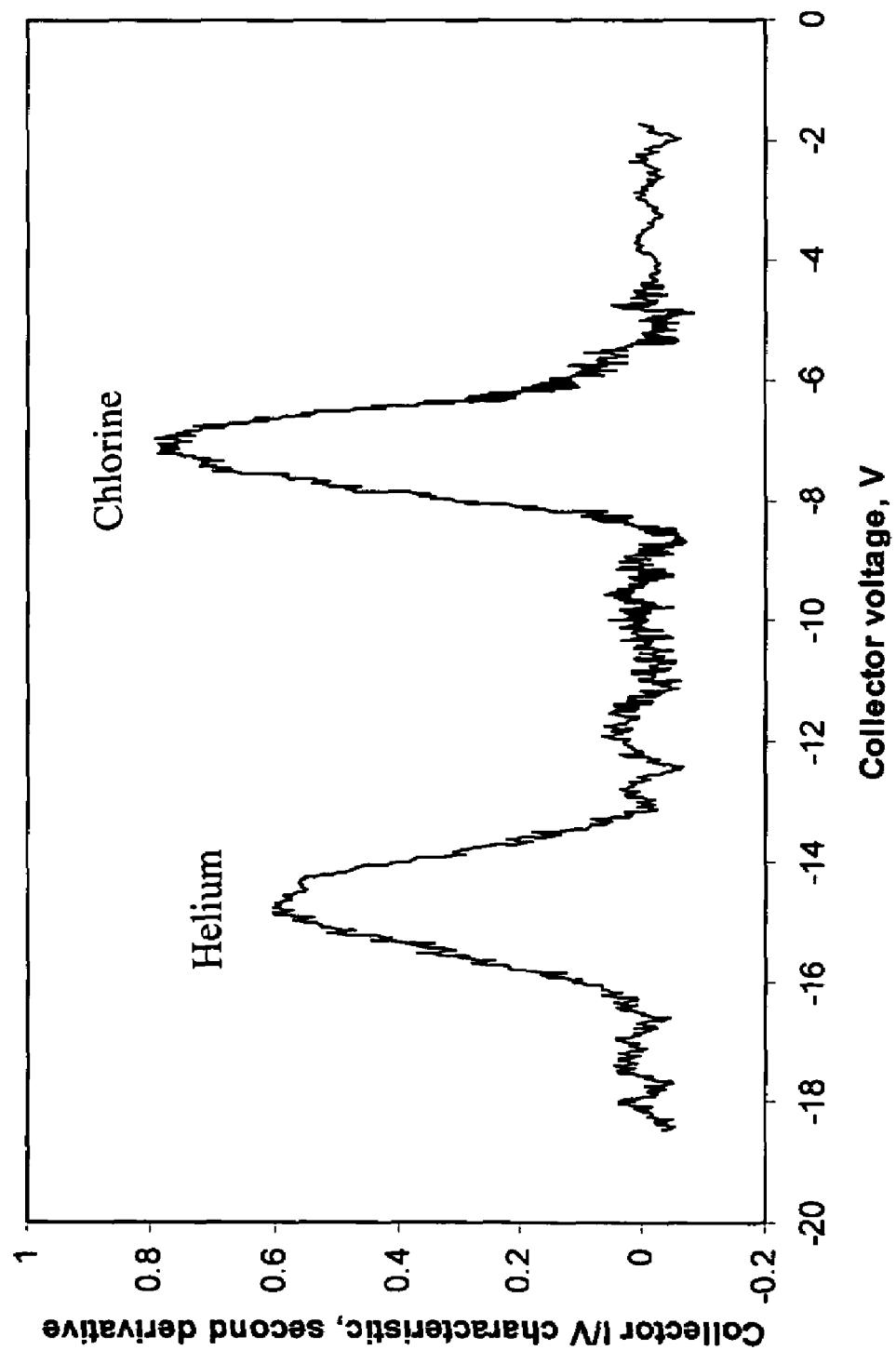
FIG. 8 illustrates a typical electron spectrum display developed by the FIG. 7 gas analyzer apparatus.

Referring to FIG. 7, a gas detection and identification apparatus, constructed in accordance with the present invention, includes a gas detector 40 of the type illustrated in FIGS. 1 through 6 and described above. Specifically, gas detector 40 includes an elongated tube, means at a first end of the elongated tube for receiving in a through bore extending through the elongated tube a flow of a mixture of a carrier gas and an analyte gas, means at a second end of the elongated tube for exhausting from the through bore the flow of the mixture of the carrier gas and the analyte gas, pair of excitation electrodes, and an electron collector electrode.

The source of the flow of the mixture of the carrier gas and the analyte gas received by gas detector 40 is, for the embodiment of the present invention illustrated in FIG. 7 and being described, a gas chromatograph 42 composed of a gas sampling unit 44 and a capillary column 46. The carrier gas can be an inert gas such as helium, argon, neon or xenon and the analyte gas can be one or more gases present in a specimen introduced into gas chromatograph 42 that exit capillary tube 46 of the gas chromatograph separated in time in the usual manner. The gas flow through gas detector 40 is exhausted to a suitable waste container that is not shown. The analyte gases used in describing the operation of the present invention are chlorine and ammonia.

The FIG. 7 a gas detection and identification apparatus also includes an excitation voltage source 48 connected to the excitation electrodes, represented by terminals 50 and 52, of gas detector 40 for applying an excitation voltage between the excitation electrodes. A computer 54 controls operation of excitation voltage source 48. In accordance with Penning Ionization Electron Spectroscopy (PIES), the excitation voltage applied between the excitation electrodes excites the mixture of the carrier gas and the analyte gas supplied to gas detector 40 to ionize the mixture of the carrier gas and the analyte gas and transform the mixture of the carrier gas and the analyte gas into a plasma that contains excited atoms and molecules of the carrier gas and electrons at various excitation levels released from the analyte gas that travel in the plasma and with which the excited atoms and molecules of the carrier gas collide.

The FIG. 7 gas detection and identification apparatus also includes an electron collection voltage source/current measurement circuit 56 connected to the electron collector electrode, represented by terminal 58, of gas detector 40 for applying an electron collection voltage that varies in level over time to the electron collector electrode. Computer 54 also controls operation of electron collection voltage source/current measurement circuit 56. Further in accordance with Penning Ionization Electron Spectroscopy (PIES), the electron collection voltage applied to the electron collector electrode selectively, at particular times, allows those electrons traveling in the plasma that have excitation levels exceeding the level of the electron collection voltage applied to the electron collector electrode at the particular times to reach the electron collector electrode. The current through the electron collector electrode resulting from the electrons in the plasma that reach and are collected by the electron collector electrode is supplied to electron collection voltage source/current measurement circuit 56 where the current through the electron collector electrode is measured at particular times for the particular electron collection voltages applied to the electron collector electrode at the particular times. The measured current is supplied to computer 54 which develops a spectrum proportional to the number of electrons collected at different levels of the electron collection voltage applied to electron collector electrode 58, such as the electron spectrum illustrated in FIG. 8.

Each gas, carrier or analyte, exiting capillary tube 46 of the gas chromatograph has a distinct electron spectrum that identifies the gas. The peak identified by the notation helium indicates that helium, as a carrier gas for example, is in the gas mixture exiting capillary tube 46 and the peak identified by the notation chlorine indicates that chlorine, for example, as an analyte gas, is in the gas exiting the capillary tube. The presence of ammonia, a second analyte gas for example in the gas exiting capillary tube 46, would be indicated by a different electron spectrum developed subsequent to the development of the FIG. 8 electron spectrum because ammonia would exit capillary tube 46 subsequent to chlorine exiting the capillary tube. For ammonia, the electron spectrum would have two peaks.

Figure 9A:
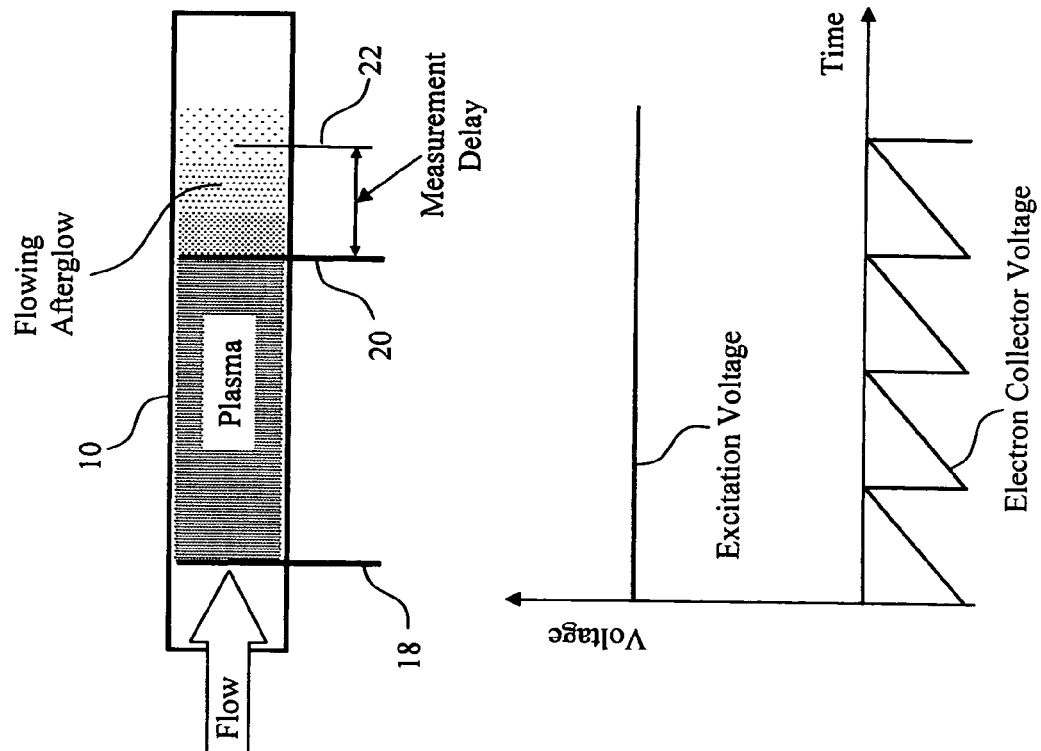
FIGS. 9A and 9B include timing diagrams of the excitation voltages and the electron collector voltages applied, respectively, to the excitation electrodes and the electron collector electrodes of the FIG. 1 and FIG. 5 embodiments of the present invention that are illustrated schematically above the respective timing diagrams.

FIG. 9A includes a timing diagram of the excitation voltage applied to excitation electrodes 18 and 20 and the electron collection voltage applied to electron collector electrode 22 of the FIG. 1 embodiment of the present invention that is illustrated schematically above the timing diagram. The excitation voltage is applied periodically to excitation electrodes 18 and 20 over fixed periods of time that are separated in time in accordance with standard Penning Ionization Electron Spectroscopy (PIES) operation. The electron collection voltage is applied periodically to electron collector electrode 22 over fixed periods of time that are separated in time in accordance with standard Penning Ionization Electron Spectroscopy (PIES) operation. Specifically, the electron collection voltage is applied after the expiration of fixed periods of time following removals of the excitation voltage. Further in accordance with standard Penning Ionization Electron Spectroscopy (PIES) operation, as indicated by the notation Scanning Step, the level of the electron collection voltage increases with each application of the electron collection voltage and each application of the electron collection voltage is delayed a prescribed period of time after the excitation voltage is removed to permit a state of the plasma, known as "afterglow," to be developed before the current through electron collector electrode 22 is measured. This delay in current measurement is identified by the notation Measurement Delay. The current through electron collector electrode 22, resulting from the electrons in the plasma afterglow that reach and are collected by electron collector electrode, is supplied to electron collection voltage source/current measurement circuit 56 in FIG. 7 where the current through the electron collector electrode during afterglow is measured. Such current measurements are made during plasma afterglow and are dependent on the level of the electron collection voltage applied to the electron collector electrode at the particular times. In this manner, the full spectrum of electrons collected at each level of the electron collection voltage applied to electron collector electrode 22 is developed after the highest level electron collection voltage has been applied to the electron collector electrode.

Figure 9B:
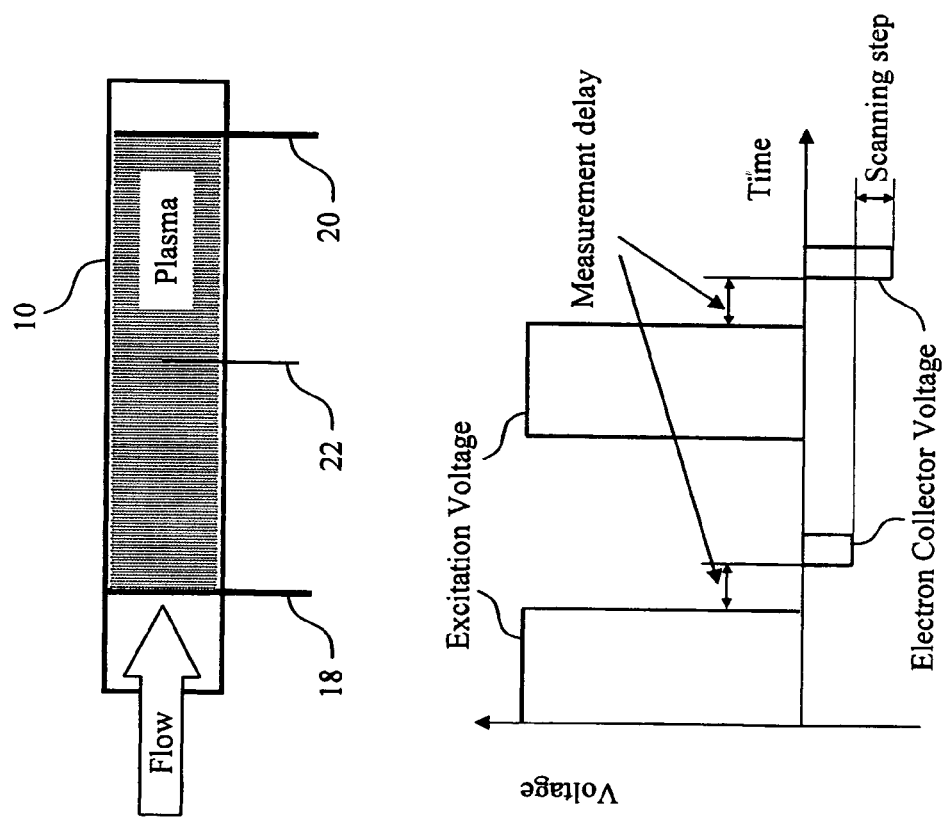

FIG. 9B includes a timing diagram of the excitation voltage applied to excitation electrodes 18 and 20 and the electron collection voltage applied to electron collector electrode 22 of the FIG. 5 embodiment of the present invention that is illustrated schematically above the timing diagram. In contrast to the FIG. 1 embodiment of the present invention, the excitation voltage is applied steadily to excitation electrodes 18 and 20 in the FIG. 5 embodiment of the present invention. The electron collection voltage, in the form of a repetitive ramp, is applied to electron collector electrode 22. In this way, the level of the electron collection voltage applied to electron collector electrode 22 increases. The Measurement Delay in the FIG. 5 embodiment of the present invention is achieved by the time required for the plasma to flow from between excitation electrodes 18 and 20 to a region downstream from the downstream excitation electrode, namely excitation electrode 20, where electron collector electrode 22 is positioned. This region is identified as Flowing Afterglow in FIG. 9B. The current through electron collector electrode 22, resulting from the electrons in the plasma that reach and are collected by the electron collector electrode, is supplied to electron collection voltage source/current measurement circuit 56 in FIG. 7 where the current through the electron collector electrode is measured. In the FIG. 5 embodiment of the present invention, the full spectrum of electrons collected by the electron collector electrode is developed over one cycle of the ramp voltage applied to electron collector electrode 22. The timing and control circuitry for applying the excitation voltage to the excitation electrodes and the electron collection voltage to the electron collector electrode is simpler for the FIG. 5 embodiment of the present invention than for the FIG. 1 embodiment of the present invention and the full spectrum of electrons collected by the electron collector electrode is developed more quickly by the FIG. 5 embodiment of the present invention than by the FIG. 1 embodiment of the present invention.

Although the invention is illustrated and described herein with it reference to specific embodiments, the invention is not intended to be limited to the details shown. Rather, various modifications may be made in the details within the scope and range of equivalents of the claims and without departing from the invention.

What is claimed:

1. A gas detector comprising:
   an elongated tube having:
   (a) means for receiving a flow of a mixture of a carrier gas and an analyte gas,
   (b) means for exhausting the flow of the mixture of the carrier gas and the analyte gas, and
   (c) a through bore free of recesses extending between said means for receiving the flow of the mixture of the carrier gas and the analyte gas and said means for exhausting the flow of the mixture of the carrier gas and the analyte gas; and
   a pair of excitation electrodes and an electron collector electrode:
   (a) mounted to said elongated tube at selected locations along the length of said elongated tube,
   (b) exposed to the flow of the mixture of the carrier gas and the analyte gas through said through bore,
   (c) said pair of excitation electrodes adapted for connection to a source of excitation voltage for:
      (1) exciting the mixture of the carrier gas and the analyte gas, and
      (2) transforming the mixture of the carrier gas and the analyte gas into a plasma that contains:
         (i) excited atoms and molecules of the carrier gas, and
         (ii) electrons at various excitation levels released from the analyte gas that travel in the plasma, and
   (d) said electron collector electrode adapted for connection to a source of electron collection voltage that varies in level over time for selectively collecting at particular times those electrons traveling in the plasma that have excitation levels exceeding the levels of the electron collection voltage applied to said electron collector electrode at the particular times.

2. A gas detector according to claim 1 wherein said electron collector electrode is mounted between said excitation electrodes.

3. Gas detection and identification apparatus comprising;
   a gas detector comprising:
   (a) an elongated tube having:
      (1) means for receiving a flow of a mixture of a carrier gas and an analyte gas,
      (2) means for exhausting the flow of the mixture of the carrier gas and the analyte gas, and
      (3) a through bore free of recesses extending between said means for receiving the flow of the mixture of the carrier gas and the analyte gas and said means for exhausting the flow of the mixture of the carrier gas and the analyte gas, and (b) a pair of excitation electrodes and an electron collector electrode:
  (1) mounted to said elongated tube at selected locations along the length of said elongated tube, and
  (2) directly exposed to the flow of the mixture of the carrier gas and the analyte gas through said through bore;

an excitation voltage source connected to said excitation electrodes for applying an excitation voltage between said excitation electrodes to:
  (a) excite the mixture of the carrier gas and the analyte gas, and
  (b) transform the mixture of the carrier gas and the analyte gas into a plasma that contains:
    (1) excited atoms and molecules of the carrier gas, and
    (2) electrons at various excitation levels released from the analyte gas that travel in the plasma;

an electron collection voltage source connected to said electron collector electrode for applying an electron collection voltage that varies in level over time to said electron collector electrode to selectively collect at particular times those electrons traveling in the plasma that have excitation levels exceeding the level of the electron collection voltage applied to said electron collector electrode at the particular times; and means responsive to the electrons collected at said electron collector electrode for developing a spectrum of the electrons collected at different voltage levels of the electron collection voltage applied to said electron collector electrode.

4. Gas detection and identification apparatus according to claim 3 wherein said electron collector electrode is mounted between said excitation electrodes.

5. Gas detection and identification apparatus according to claim 4 wherein:
  (a) the excitation voltage is applied periodically over fixed periods of time, and
  (b) the electron collection voltage is applied:
    (1) periodically over fixed periods of time after the expiration of fixed periods of time following removals of the excitation voltage, and
    (2) at increasing voltage levels.

6. A method for detecting and identifying gases comprising the steps of:
  receiving a mixture of a carrier gas and an analyte gas;
  applying steadily throughout a detection time period an excitation voltage to a pair of excitation electrodes for exciting the mixture of the carrier gas and the analyte gas and transforming the mixture of the carrier gas and the analyte gas into a plasma that contains excited atoms and molecules of the carrier gas and electrons at various excitation levels released from the analyte gas that travel in the plasma;
  applying a ramp electron collection voltage that increases in level to an electron collector electrode for selectively collecting at particular times electrons traveling in the plasma that have excitation levels exceeding the level of the electron collection voltage applied to said electron collector electrode at the particular times;
  developing a spectrum of the number of electrons collected by said electron collector electrode at different voltage levels of the electron collection voltage applied to said electron collector electrode; and
  exhausting the flow of the mixture of the carrier gas and the analyte gas.

7. Gas detection and identification apparatus comprising;
  a gas detector comprising:
    (a) an elongated tube having:
      (1) means for receiving a flow of a mixture of a carrier gas and an analyte gas,
      (2) means for exhausting the flow of the mixture of the carrier gas and the analyte gas, and
      (3) a through bore free of recesses extending between said means for receiving the flow of the mixture of the carrier gas and the analyte gas and said means for exhausting the flow of the mixture of the carrier gas and the analyte gas, and
    (b) an upstream excitation electrode, a downstream excitation electrode, and an electron collector electrode:
      (1) mounted to said elongated tube at selected locations along the length of said elongated tube with said electron collector electrode mounted between the downstream excitation electrode and said means for exhausting the flow of the mixture of the carrier gas and the analyte gas, and
      (2) exposed to the flow of the mixture of the carrier gas and the analyte gas through said through bore;
  excitation voltage source means connected to said excitation electrodes for steadily applying an excitation voltage between said excitation electrodes to:
    (a) excite the mixture of the carrier gas and the analyte gas, and
    (b) transform the mixture of the carrier gas and the analyte gas into a plasma that contains:
      (1) excited atoms and molecules of the carrier gas, and
      (2) electrons at various excitation levels released from the analyte gas that travel in the plasma;
  electron collection voltage source means connected to said electron collector electrode for applying a ramp electron collection voltage that increases in level over time to said electron collector electrode to selectively collect at particular times those electrons traveling in the plasma that have excitation levels exceeding the level of the electron collection voltage applied to said electron collector electrode at the particular times; and
  means responsive to the electrons collected at said electron collector electrode for developing a spectrum of the electrons collected at different voltage levels of the electron collection voltage applied to said electron collector electrode.

* * * * *